United States Patent [19]

Nomura et al.

[11] 4,140,021

[45] Feb. 20, 1979

[54] METHOD AND DEVICE FOR MONITORING SUPERCONDUCTING SYSTEM

[75] Inventors: Harehiko Nomura, Musashi-Murayama; Kiyoshi Takahisa, Tokyo, both of Japan

[73] Assignees: Agency of Industrial Science & Technology; Ministry of International Trade & Industry, both of Tokyo, Japan

[21] Appl. No.: 841,107

[22] Filed: Oct. 11, 1977

[30] Foreign Application Priority Data

Oct. 8, 1976 [JP] Japan .............................. 51-120279
Oct. 26, 1976 [JP] Japan .............................. 51-127785

[51] Int. Cl.² ............................................ G01N 29/04
[52] U.S. Cl. ..................................... 73/587; 307/306; 361/19
[58] Field of Search ............... 73/88 R, 587; 307/306; 361/19, 141

[56] References Cited

U.S. PATENT DOCUMENTS

| 3,214,637 | 10/1965 | Persson ................................. 361/19 |
| 3,579,035 | 5/1971 | Burnier et al. .................. 307/306 X |
| 3,875,381 | 4/1975 | Wingfield et al. ................. 73/587 X |
| 4,009,463 | 2/1927 | Vercellotti ............................. 73/587 |

OTHER PUBLICATIONS

Dunegan et al., "Acoustic Emission" in Research/Development, 5/71, pp. 20-23.

Primary Examiner—Herbert Goldstein
Attorney, Agent, or Firm—Oblon, Fisher, Spivak, McClelland & Maier

[57] ABSTRACT

The explosion or destruction of a superconducting system which may occur when an abnormal state arises in any part of the system if allowed to develop into a catastrophic quenching is prevented by providing the system with an acoustic wave detecting device adapted to detect the acoustic waves emitted upon occurrence of the abnormal state, analyze the acoustic waves detected in the form of signals to determine the extent of the abnormal state, foretell stepwise the approach of catastrophic quenching and, on the basis of the data thus obtained, effect proper feedback to the system.

9 Claims, 22 Drawing Figures

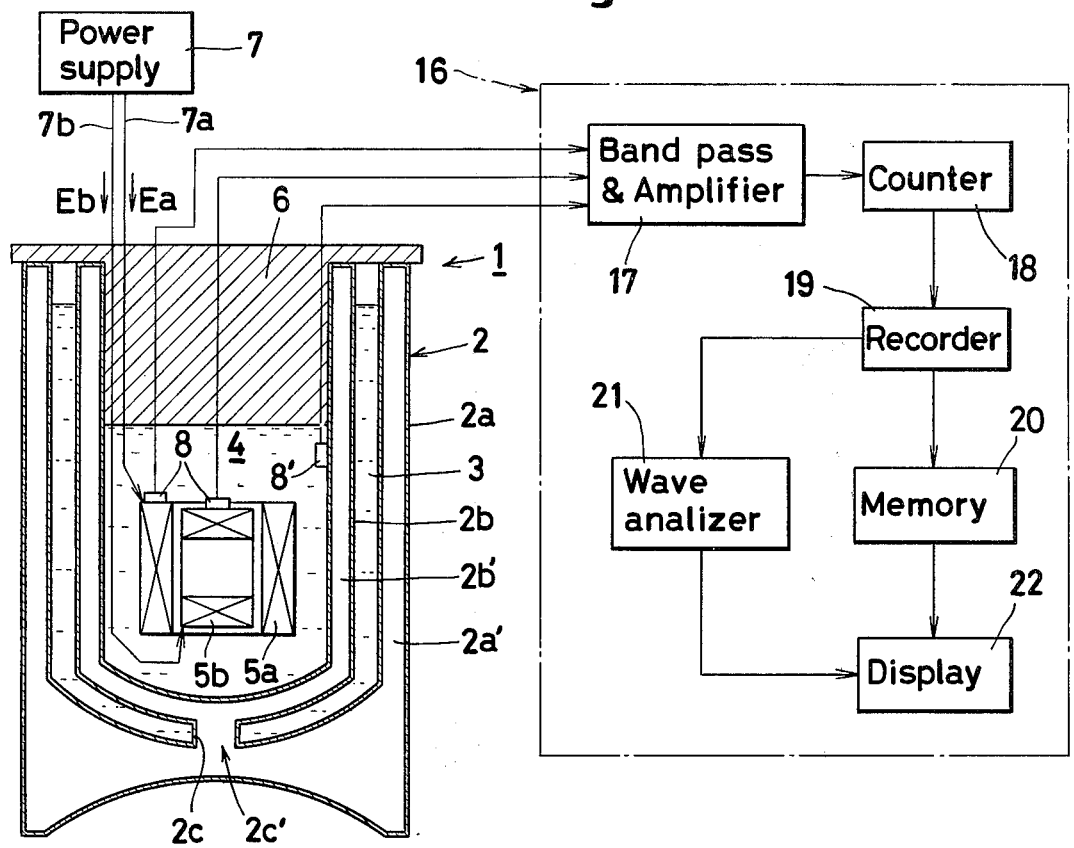
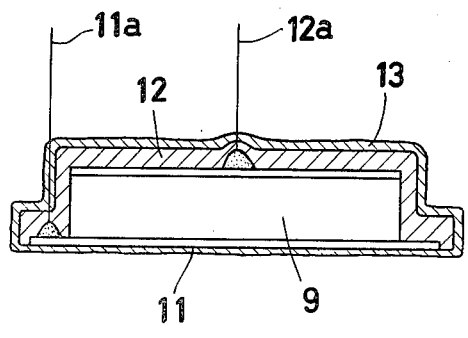
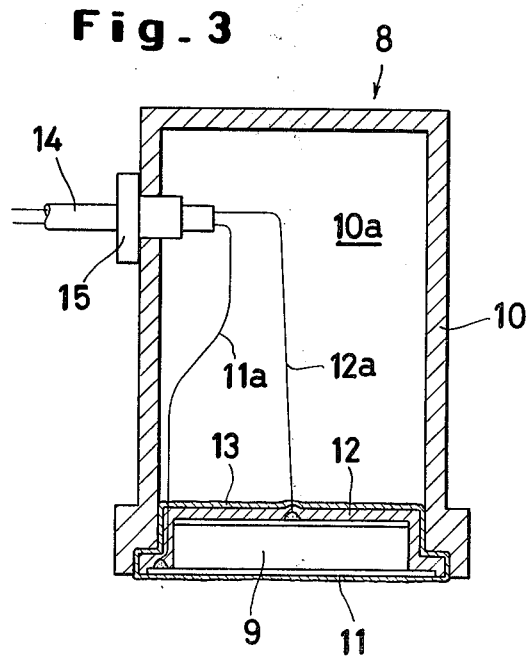

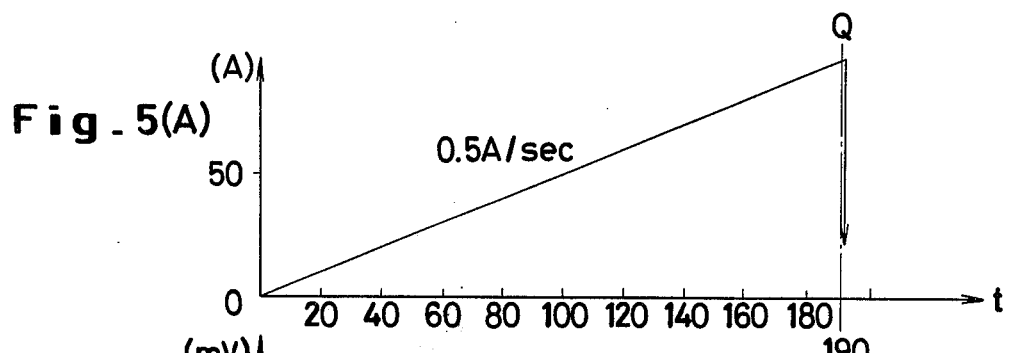
Fig.5(A)
Fig.5(B)
Fig.5(C)
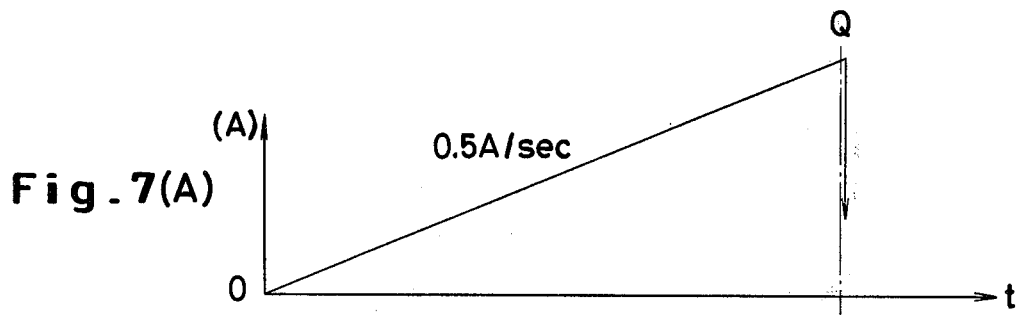
Fig.7(A)
Fig.7(B)
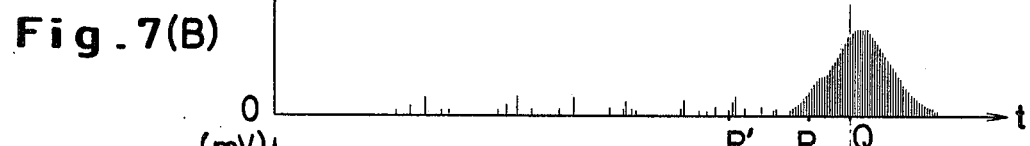
Fig.7(C)
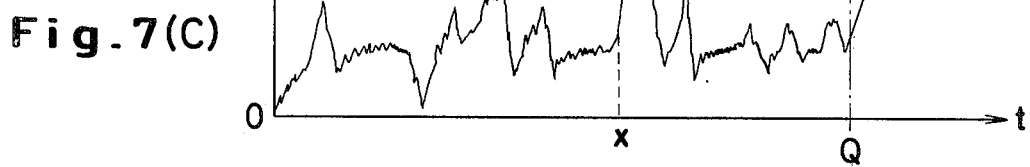

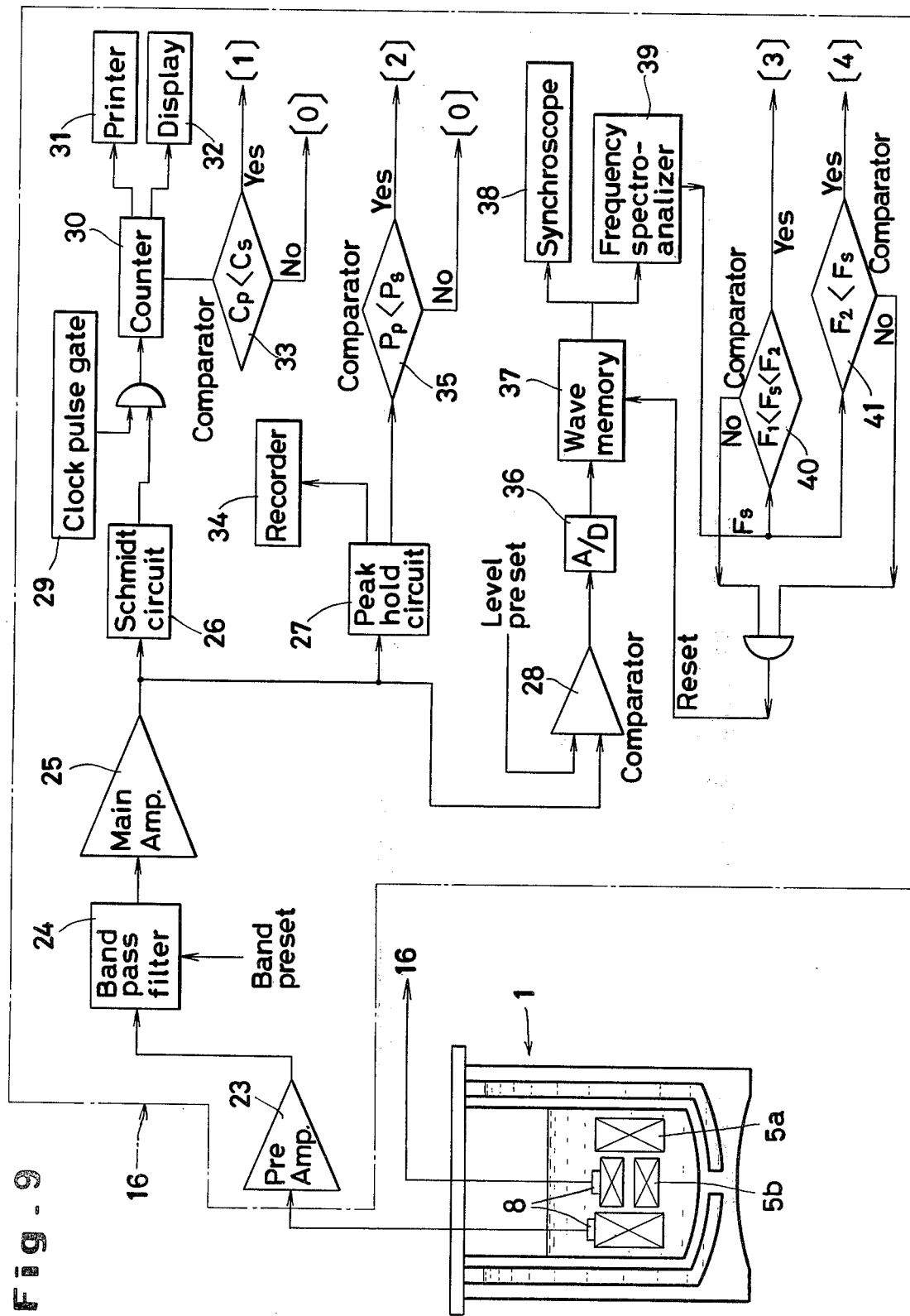

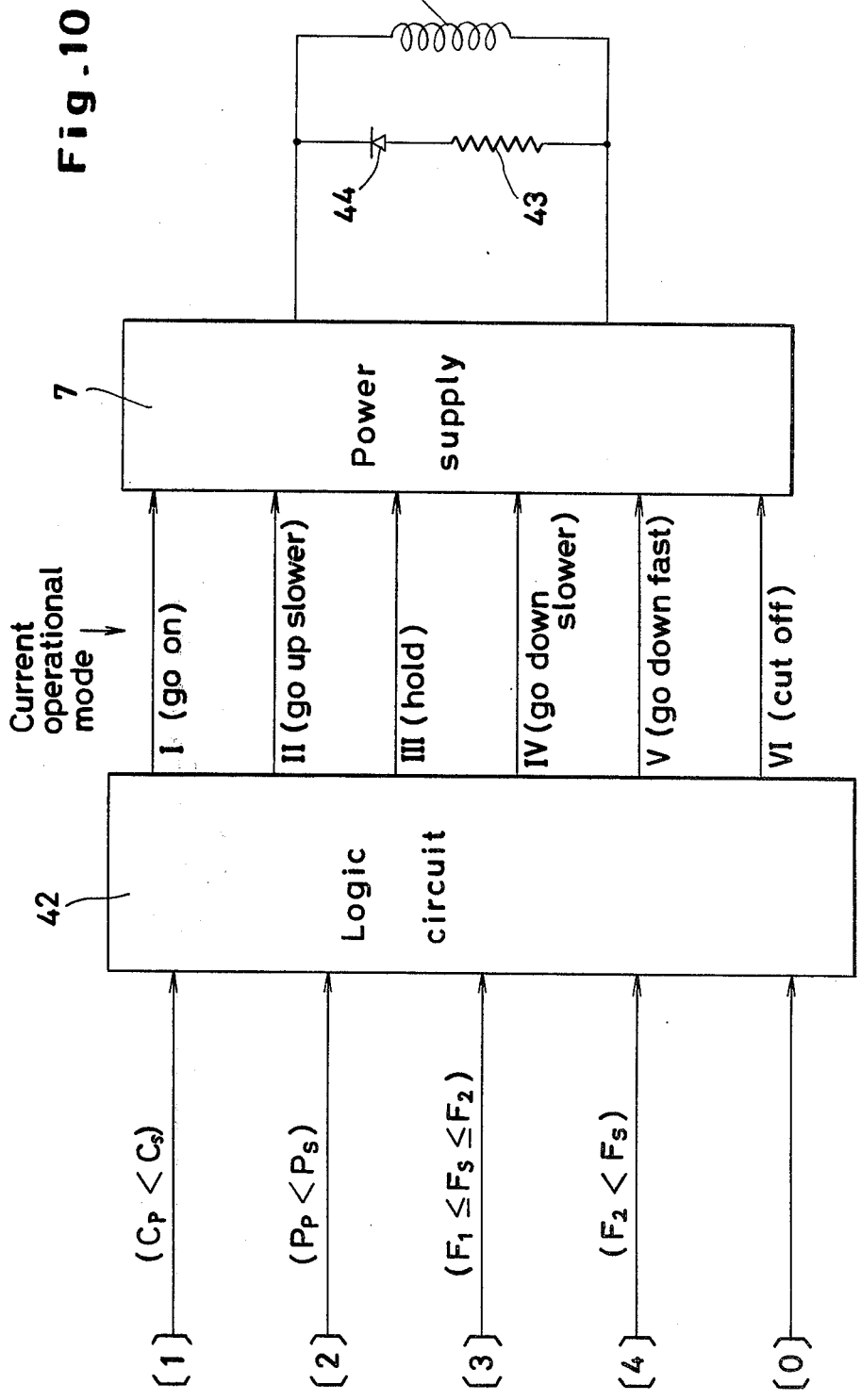

METHOD AND DEVICE FOR MONITORING SUPERCONDUCTING SYSTEM

BACKGROUND OF THE INVENTION

This invention relates to a method and device for the monitoring, in the comprehensive sense, of the whole of a superconducting system using as its principal component a superconducting functional element such as a superconducting electromagnet and incorporating a supporting structure therefor, i.e. for collective monitoring of the condition of the operation of the system, the condition under which the system is maintained in an extremely cooled state suitable for operation, and the condition under which the cooling of the system to the said extremely cooled state suitable for operation proceeds (hereinafter referred to as "precooling process"). It has heretofore been impossible to carry out comprehensive monitoring of a superconducting system in the manner described above because of the lack of an effective monitoring method capable of ensuring uniformized cooling for the system in the precooling process. The conventional art available for the monitoring of a system in operating condition has invariably relied solely upon a method involving the measurement of magnet voltage which has various disadvantages as will be described afterward. Thus, the monitoring of the operating condition obtained thereby has been quite unstable even during the most important phase of the operation.

As is universally known, a superconducting system is often used for the purpose of internally storing or conveying a high magnitude of energy and relies on a functional element such as, for example, a superconducting electromagnet or superconducting cable which is incorporated therein. If, during the operation of the system, a transfer from superconductivity to normal conduction (the S-N transition) takes place even partially in the superconducting functional element, the phenomenon of this transfer will, in the neighborhood of the critical point at which said transfer takes place, occur in the form of a positive feedback such as, for example, where heat generation excites further heat generation, no matter whether the said transfer may arise because of the influence of magnetic field, electric current or temperature. Once there is developed an unstable state, it tends to proceed frequently at a high velocity because of catastrophic quenching, a phenomenon in which the transfer of the state of superconductivity to that of normal conduction proceeds at a high rate of speed. Because of rapid growth of the unstable state coupled with the high magnitude of energy involved as mentioned above, the superconducting functional element undergoes an unexpected thermal load and a consequent breakage, with the possible result that the entire system may explode.

The recent trend has been toward gradual growth in the capacity of superconducting functional elements such as superconducting electromagnets and the total energy accumulated in the form of magnetic energy in these elements often reaches enormous magnitudes on the order of from megajoules to gigajoules. Thus, the destruction incurred by the functional elements by the S-N transition occurs in the form of an explosion so that anything in the surrounding is exposed to extreme danger. It is, therefore, highly desirable for the superconducting functional element in its operating condition to retain the superconducting state safely. For this reason, it is of very importance that whenever even a slight deviation from the superconducting state occurs in any part of the system or the functional element, it should be immediately detected in order to determine the existence of a dangerous state or the state immediately preceding the dangerous state. Generally the characteristic of the superconductor is such that its thermodynamically intrinsic critical values such as critical magnetic field, critical current and critical temperature can be determined statically based on the kind of material from which the superconductor is made. In various actually used superconducting devices, however, these critical values are vary greatly from one device or functional element to another by more practical and dynamic factors such as, for example, the difference in the manner of excitation in the case of a superconducting electromagnet, interaction with an adjacently located separate superconducting electromagnet, difference in structural sensitivity due to difference in physical structure and, in particular, difference in the manner and state of cooling.

In monitoring the superconducting devices of such nature, therefore, one cannot solely rely upon purely academic theories in the measurement of static critical values. At least in foretelling the danger described above, all the devices in the superconducting system must be kept under constant watch while they are in actual operation.

Heretofore, a method involving the measurement of voltage has been the only measure available for the detection of abnormal phenomenon during the operation of the system, which, if left to take its own course, will result in catastrophic quenching. This method effects the detection of such a phenomenon by amplifying a variation in the voltage which occurs when a transition from the state of superconductivity to that of normal conduction gives rise to a change in the resistance within the functional element. This method, however, has various defects such as are enumerated hereinafter by way of example and are encountered in the operation of a superconducting electromagnet serving as a functional element.

(i) If the sensitivity to voltage is enhanced for the purpose of clearly detecting at an initial stage the phenomenon likely to result in catastrophic quenching, it is quite likely that the measuring instrument will succeed in picking up only the minute dynamic variations in the magnetic flux generated in the superconducting electromagnet itself in the course of operation and, contrary to the intended purpose, only the background noise will be detected while any electric potential of a lower level than the noise will be hidden from measurement thereby. Besides, such an enhanced sensitivity to voltage tends to impair the stability of the measuring system itself. Thus, the enhancement of sensitivity is likely to prove harmful rather than helpful.

(ii) If a variable coil is electromagnetically connected to the superconducting electromagnet in use with a view to offsetting the electromotive force generated by inductance in the electromagnet so as to permit zero-point measurement indispensable for the measurement of voltage, the magnetic flux cannot always be expected to function exactly with geometric symmetry. In the case where a plurality of superconducting electromagnets are disposed within the entire system, there is a possibility that the zero-point adjustment to be effected on the electromagnets in use will be affected by the fluxes of other electromagnets located nearby and the desired cancellation of the electromotive force will not be obtained completely. In an extreme case, the unwanted effect of such adjacently located electromagnets could cause an error in the detection of voltage.

(iii) Direct detection of a loss of stability due to the occurrence of diamagnetic current or shielding current within the system is essentially impracticable because the voltage consequently produced cannot be detected at the terminal.

(iv) Although one can definitely tell that an abnormal state occurring somewhere in the system has developed into catastrophic quenching, he has no alternative but to rely on a number of detecting terminals disposed effectively in advance in the relevant electromagnet to ensure recognition of the precise position of the abnormal state, namely, to permit safe pinpointing of the abnormal state within the system. Such provision of detecting terminals makes the construction and actual fabrication of the electromagnet quite complicated.

(v) The method involving the measurement of voltage is such that even when a transition from the superconducting state to that of normal conduction is detected thereby, catastrophic quenching still cannot be prevented because the transition often proceeds too rapidly. The only measure that can be taken by an operator for repressing the rapid growth of the transition is to cut off the flow of electric current. In a superconducting system, this discontinuation of the current flow represents an instantaneous nullification of its function. Such an instantaneous stop of the system entails various problems.

In the light of the various disadvantages enumerated above, it is totally unsafe to rely solely upon any method involving the measurement of voltage such as has been adopted to date for the detection states preceding catastrophic quenching in the functional element within the superconducting system. The result of detection by such a method so much is affected by the various indefinite factors involved as described above that the early stages of the abnormal state which develops into catastrophic quenching cannot be detected.

Perfection of a satisfactory method for monitoring the superconducting system under its operating condition has been much desired. Generally in a superconducting system, in addition to the importance attached to the detection of early signs of catastrophic quenching in the functional element, the dimensional increase of the system as a whole has made it extremely important to ensure uniformization of the cooling of the component elements of the system, namely the functional element, its housing and those members which serve to support the functional element with reference to the housing and consequently permit required assembly of the superconducting system in the mechanical sense. Thus, it is necessary to adopt additionally a method for monitoring the system with respect to the condition of cooling, particularly for the purpose of detecting any loss of balance in the overall cooling of the system which tends to occur in the course of precooling, because the said loss of balance may possibly upset the equilibrium in shrinking thermal stress and consequent deformative strain in the component elements of the system, impart adverse effects upon the operation of the functional element and mechanically damage the container (occasionally giving rise to fracture through the development of cracks).

An object of the present invention is to provide a method and device for the monitoring of a superconducting system, which permits detection of incipient S-N transition, or even of states preceding the incipient state, occurring in the functional element of the superconducting system.

Another object of the present invention is to provide a method and device for the monitoring of a superconducting system, which enables a sign preceding the occurrence of an abnormal state in the entire superconducting system to be detected with high accuracy during the operation of the system or during the precooling of the system without being adversely affected by the magnetic field of the superconducting system being monitored.

SUMMARY OF THE INVENTION

To accomplish the objects described above according to the present invention, there is provided a method for the monitoring of a superconducting system, which method comprises causing an acoustic wave signal emitted upon occurrence of an abnormal state in the superconducting system to be detected by means of at least one acoustic wave detector provided on said superconducting system and subsequently measuring the frequency, intensity, frequency of occurrence, wave forms, etc. of the detected acoustic wave signal for thereby rating the abnormal state of the superconducting system. If said abnormal state is judged to threaten no immediate danger, the operation of the superconducting system is left to proceed continuously. If the abnormal state is judged to have a possibility of being further aggravated to a dangerous level, the current rate of increasing the supply of electric current is properly lowered without interrupting the operation of the superconducting system. If the detection of the acoustic wave signal indicative of an abnormal state is made while the superconducting system is being cooled to extremely low temperatures, the detected signal is similarly analyzed and, depending on the result of this analysis, the cooling of the system is continued or stopped or slowed down.

As described above, the method and device of the present invention provides constant monitoring of the operating condition of the superconducting system so as to detect any sign of abnormality of the operation of the system amply before the abnormal state has fully grown to a point where the system undergoes catastrophic quenching and possible explosive destruction. Upon the early detection of an abnormal state, a necessary countermeasure can be taken to eliminate the abnormal state and permit safe continuation of the operation of the superconducting system.

The other objects and characteristic features of this invention will become apparent from the detailed description of the invention to be given hereinafter with reference to the accompanying drawing.

BRIEF EXPLANATION OF THE DRAWING

FIG. 1 is a schematic structural diagram illustrating one embodiment of the present invention.

FIG. 2 is a sectioned view of one example of the acoustic wave detecting element to be used in the present invention.

FIG. 3 is a sectioned view of an acoustic wave detector incorporating therein the element of FIG. 2.

FIG. 5(A) is a graph showing the driving current characteristics as exhibited when one of the electromagnets in the system of FIG. 1 is left to undergo catastrophic quenching.

FIG. 5(B) is a graph showing the characteristics of acoustic wave signal detection as exhibited under the condition touched upon above.

FIG. 5(C) is a graph showing the detection voltage characteristics as exhibited when the conventional method involving the measurement of voltage is applied under said condition.

FIG. 7(A) is a graph showing the driving current characteristics as exhibited when both the electromagnets in the system of FIG. 1 are left to undergo catastrophic quenching.

FIG. 7(B) is a graph showing the characteristics of acoustic wave signal detection as exhibited under the condition touched upon above.

FIG. 7(C) is a graph showing the detection voltage characteristics as exhibited when the conventional method involving the measurement of voltage is applied under said condition.

FIG. 9 is a circuit view showing one example of a circuit system of the present invention for monitoring the superconducting system.

FIG. 10 is a circuit view showing one example of a circuit system for controlling electric power supplied to the superconducting system by means of the output obtained from the circuit system of FIG. 9.

DESCRIPTION OF THE PREFERRED EMBODIMENT

Figure 4:
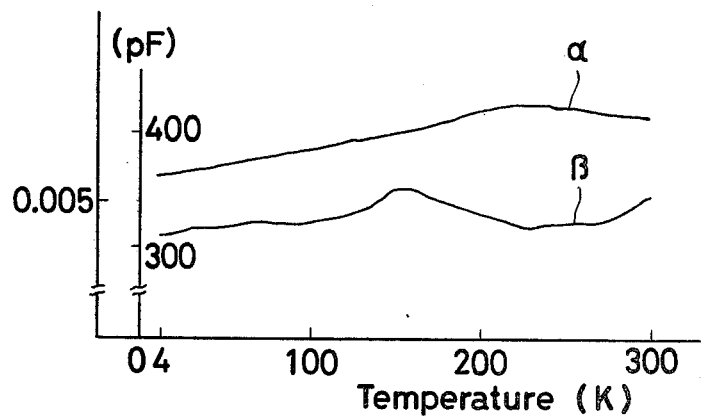
FIG. 4 is a graph showing the electric characteristics vs. temperature of the acoustic wave detector of FIG. 3.

First, the points which were taken into consideration in a scientific inquiry into the detection of the S-N transition which is apt to induce the phenomenon of quenching will be outlined.

Generally, the characteristics of the phenomenon of superconductivity is such that when a given system is cooled extremely to a point where the part of electrons in the system come to move at a phase velocity smaller than the speed of sound, these electrons can be regarded as assuming a state no longer capable of being deprived of their momentum and energy with reference to their lattices, whereby no absorption of acoustic waves can be obtained any longer in the superconductive state from the standpoint of the acoustic waves to be generated by some thermal factor. The phenomenon thus brought about is completely the opposite to the phenomenon of absorption of acoustic waves which occurs in the state of normal conduction.

By reviewing critical phenomena from a new angle totally different from the angle of the conventional investigation while attaching particular attention to such acoustic waves as are caused by the interaction of quasi-corpusculated photons and electrons, the underlying essence of the phenomenon of superconductivity has been elucidated from the following results of theoretical and empirical studies.

A superconductor of the second kind which is finding prevalent acceptance for use in superconducting electromagnets is cited herein by way of example. Even at extremely low temperatures which permit the superconductor to assume the superconducting state, there still exist a series of lattices embracing the domains of normal conduction at the core. Owing to the series of lattices thus retained in the system, magnetic induction is stopped even if the so-called pinning force originating in the state of normal conduction functioning as the core of such lattices encourages magnetization. As a result, perpetual flow of electric current becomes possible. This pinning force, however, has its own limit of stress because it functions in opposition to the universally known Lorentz force. This implies that a trend toward more stable distribution of stress may result in mitigation of stress. What has been actually ascertained about this point by the present inventors is that acoustic waves or ultra-acoustic waves (possibly reaching the order of several mega-hertzes) are emitted as part of the strain-energy and there exists a definite correlation between the intensity and waveform of the emission and the stability of the superconducting electromagnet.

This means that the catastrophic phenomenon of quenching can be detected while it is still in the incipient stage or even in a stage which can be considered a mere sign preceding the incipient stage if the acoustic wave signal generated or emitted when the S-N transition occurs even partially in the superconductor can be recognized and, especially, if it can be recognized still in the very early and feeble stage.

The monitoring method to which the present invention is directed is primarily based on this principle. As substantially demonstrated in the examples cited afterward, even at extremely low temperatures, various forms of information such as the magnitude of load and the phase of the acoustic waves (including ultra-acoustic waves) emitted owing to the aforementioned S-N transition can be detected by virtue of this principle.

Now that the fundamental principle of this invention concerning the monitoring of the phenomenon of quenching has been described, the auxiliary function for the detection or measurement of the aforementioned unbalance in the cooling condition and the deformative strain due to the thermal contraction at the time of cooling will be described.

It has been confirmed that elastic stress-strain is produced when there occurs uneven thermal contraction while the functional elements such as a superconducting electromagnet (including the superconductor and its component members) and the container are being cooled and that a part of the energy produced in that case is emitted in the form of acoustic waves (including ultra-acoustic waves).

If a method is established for continuously monitoring the superconducting system by detecting the acoustic waves thus emitted, analyzing the frequency spectrum of the waves and determining the intensity of emission and the frequency and shape of the emitted waves, it will prove highly significant as an approach for quantitative determination. It will also serve to promote the uniformization of the speed of cooling and even the uniformization of the cooling condition of the individual component members from the overall point of view, and consequently overcome the various disadvantages issuing from the aforementioned unbalanced cooling. It goes without saying that if, in a superconducting system already cooled to an extremely low temperature sufficient to permit the motion of conduction electrons, the cooled condition is unbalanced by some external factor, the monitoring method described above is capable of detecting the occurrence of such an unbalance. In the description given above, a particularly detailed explanation has been made about the pre-cooling phase of the operation. This is because the disadvantages issuing from the loss of balance during the cooling process such as, for example, degradation of the efficiency of the functional element and breakage of the container are liable to be induced while the superconducting system is undergoing the precooling.

Now, an embodiment of this invention will be described by reference to the accompanying drawing.

The superconducting system 1 of FIG. 1 which is used for working the present invention may be any of the types already known in the art insofar as it is capable of providing the kind of monitoring aimed at by the invention. Thus, the construction of the system illustrated herein solely by way of example will be explained only briefly.

In FIG. 1, the container 2 has the structure of a vessel designed to withstand extremely low temperatures, with an inner cylindrical part 2b concentrically enclosed inside an outer cylindrical part 2a. The inner and outer cylindrical parts are connected to each other at the position 2c near the center of the bottom. At all the other positions, the inner surface of the outer cylindrical part 2a and the outer surface of the inner cylindrical part 2b are opposed to each other so as to enclose a proper space 3 therein. Thus, the two cylindrical parts 2a, 2b as a whole constitute a double-wall structure. The interiors of these cylindrical parts, namely the parts 2a' and 2b' enclosed with the inner and outer surfaces thereof and the part 2c' intervening between the opposed connecting parts 2c, are retained under a vacuum.

In the construction described above, a first toroidally wound superconducting electromagnet coil 5a is fixed at a suitable position by known suitable supporting means (not shown) inside the space 4 defined by the inner surface of the inner cylindrical part 2b and a second toroidally wound superconducting electromagnet coil 5b is disposed inside said first coil. These two coils 5a, 5b, the supporting means serving to support the two coils relative to the container and other peripheral components (not shown) are cooled with an ambient cryogenic refrigerant such as liquid helium to about 4.2° K. at which temperature the coils manifest superconductivity. The space 3 enclosed with the two cylindrical parts is generally filled with liquefied nitrogen so as to operate in conjunction with the intervening part kept under a vacuum to heat shield the entire structure from its surroundings for thereby maintaining the innermost space 4 under an extremely cooled condition. The container 2 is generally provided with a lid 6 which serves the purpose of closing the upper side of the innermost space 4. From the functional point of view, in order to allow the two coils 5a, 5b to effectively function as superconducting electromagnets under such an extremely cooled condition, it is necessary to supply driving currents Ea, Eb from the external power supply 7 to the coils 5a, 5b via the corresponding current leads 7a, 7b.

The application of the present invention to the conventional superconducting system 1 described above will now be described in terms of the monitoring method referred to earlier for the detection of abnormal states which may lead to catastrophic quenching during the operation of the superconducting electromagnetic coils 5a, 5b. (These coils are hereinafter referred to simply as "electromagnets" by in view of the dynamic condition under which they operate.)

At least one of the electromagnets 5a, 5b, and preferably both of them for the purpose of permitting direct monitoring of each, is provided with a suitable number of accoustic wave detectors 8 (one in the present embodiment) which are attached thereto at suitable positions.

The acoustic wave detector is preferably an element possessed of the ability to provide acoustic field-to-electric field conversion. For example, use of a reversible piezoelectric vibrator or a piezoelectric resonator having electrodes disposed on a wafer such as of lead titanozirconate ceramic (known as PZT) proves to be convenient. When the acoustic wave detector is immersed in liquid helium and held in intimate contact with the electromagnet maintained under extremely cooled condition, however, it may possibly fail to manifest the capacity for detection satisfactorily. By the method described below it is possible to manufacture a wide-temperature-range acoustic wave detector which stably operates at widely varying temperatures ranging from room temperature to those of the cryogenic order and which therefore serves to improve the signal-to-noise (S/N) ratio and enhance the sensitivity. The detector manufactured by this method has sufficiently high thermal stability to make the detector safe from any functional damage even when it is operated at normal temperature condition immediately after being used at extremely low temperatures.

An acoustic wave detecting sensor 9 such as of PZT material is thoroughly dried by the known vacuum-dehydration technique. The sensor 9 thus dried is molded as promptly as permissible with a high polymer resin such as, for example, a silicone resin as shown in FIG. 2, with the exception of the wave-receiving face 11. The thickness and shape of the molded layer can be freely selected by taking into account the position to be preselected for its attachment. The wave-receiving face 11 remains uncoated with the silicone resin so as to avoid otherwise possible absorption of incident sound waves. Theoretically it is nevertheless desirable for this portion of the sensor to be coated with the resin layer. It is, therefore, permissible to have the wave-receiving face 11 coated with a layer of the resin the thickness of which is amply smaller than the wavelength of the sound-wave signal the sensor is expected to respond to with sufficient sensitivity. This is because the sound-wave signal impinging upon the resin layer applied to the face reaches the wave-receiving face without being absorbed or attenuated by the coated layer when the thickness of the coated layer satisfies the aforementioned requirement.

Under no condition is it permissible to use a water-containing resin as the material for the molding. To ensure perfect absence of water, the molded layer 12 can be subjected again to drying by vacuum dehydration. The molded layer not merely prevents the sensor 9 from regaining moisture but also serves to improve the response characteristic of the sensor 9. In this respect, it may well be regarded as playing the part of a damping material which improves the frequency characteristic.

After the sensor 9 has been coated with the molded layer as described above, a film of grease 13 is applied mainly to the outer surface of the molded layer 12 for the purpose of preventing the molded layer itself and, consequently, the sensor 9 from getting wet. The material for this grease film is desired to be of a type such that when the sensor 9 is brought to extremely low temperatures, the grease film remains in a relatively stable state without sustaining cracks or other similar injuries and protects the sensor 9 against otherwise possible adverse effects of water, moisture or dew formed on the surface thereof. The experiments conducted by the inventors have shown that, of various types of greases recommended for use under vacuum conditions, silicone grease functions most advantageously and retains ample stability at extremely low temperatures.

In the case of the illustrated acoustic wave detector, the grease is applied to the wave-receiving face 11 of the sensor to ensure perfect protection of the sensor from the ambient humidity. In this case, for the same reason as mentioned above with respect to the molded layer 12, the grease ought to be spread to a thickness sufficiently smaller than the shortest wavelength in the entire frequency zone to which the sensor is expected to respond with required sensitivity, so that the grease film 13 will not cause any attenuation of the incident soundwave signal.

When the grease film 13 is applied to a wave-receiving face 11 which has already been coated with the molded layer 12, then it is desirable to keep the combined thickness of the molded layer and the grease film well below the minimum wavelength mentioned above.

The acoustic wave detecting element in its desirable form has been described. It has been ascertained, however, that quite satisfactory results are obtained as indicated afterward in the characteristic diagram of FIG. 4, simply by applying a film of grease to a thoroughly dried sensor as promptly as possible.

The sensor 9 which has undergone a thorough moisture-proofing treatment as illustrated in FIG. 2 is then encased in a suitable container 10 of a construction such as is illustrated in FIG. 3, for example. The sensor is disposed to fill up the entire opening of the container 10 and attached to the container with the aid of a suitable fastening means such as, for example, an adhesive agent (not shown). The outer wall of this container is generally made of a metallic material such as stainless steel or aluminum. At a suitable position, the outer wall contains a perforation through which the lead wires 11a, 12a from the opposite electrodes of the sensor are led out generally by means of a coaxial cable 14. In this perforation is set a suitable cable holder 15.

The acoustic wave detector 8 constructed as described above can retain its function perfectly intact when it is cooled as it is to extremely low temperatures, because the acoustic wave detecting element or sensor incorporated therein has been given a thorough moistureproof treatment as indicated previously. The interior of the air section 10a formed within the container 10 is not particularly moistureproofed, so that it is quite likely that, in the course of the cooling, drops of dew will form on the inner walls of the air section and they will eventually be deposited on the element somehow or other. Despite the adhesion of such drops of dew, there is absolutely no possibility of the element being adversely affected by the moisture. Through their experiments, the inventors have confirmed that the detector 8, when cooled to extremely low temperatures, functions perfectly with absolutely no trouble. Even if the drops of dew formed inside the air section in the course of the cooling should remain after the detector has been brought to room temperature, they have no effect whatever upon the function of the detector. This means that the transfer of this detector from the extremely cooled state to the room temperature state can be repeated many times and also that the detector can be used at any desired temperature within widely varying temperatures ranging from room temperature to extremely low temperatures of the cryogenic order. The electric characteristic diagram of FIG. 4 clearly shows that the transfer between the temperature states brings about no hindrance whatever to the function of the element.

FIG. 4 shows the characteristic diagram obtained of a detector using a sensor 9 which is coated with a film of silicone grease 13 and not protected with any molded layer 12. In the test performed to obtain said characteristic diagram, the piezoelectric vibrator of the sensor 9 was a PZT element 5 mm in diameter and 2 mm in thickness and designed for detection of acoustic waves. The curve "$\alpha$" and the curve "$\beta$" represent the results of measurement of electric capacity and electric conductance respectively, with the temperature varied from 300 K. (room temperature) to about 4 K. (extremely low temperature of cryogenic order).

As is evident from this characteristic diagram, the electric characteristics of this sensor are retained stably enough for the sensor's function to be manifested intact at all the test temperatures ranging from room temperature to extremely low temperatures. In this particular test, the electric capacity of the sensor varied slightly in the neighborhood of 400 pF throughout the entire range of test temperatures and the electric conductance was generally stable with the exception of a gentle peak appearing near the value of about 0.005 $\mu S$ a temperature of about 170 K.

The same detector was further tested to determine the extent to which the sensitivity of the sensor would be increased when it was brought to extremely lower temperatures. It was found that when the detector was placed in a cryogenic container filled with liquid helium and cooled down to about 4.2 K., it showed an improvement of about 18 dB in the S/N ratio over that of the element when held at room temperature (300 K.).

With a construction such as is illustrated in FIG. 3, there can be realized an acoustic wave detector which manifests an outstanding effect as described above. Further in the construction on FIG. 3, a desire to protect the conductor elements such as the lead wires extending from the element through the interior of the air section 10a of the container against moisture is accomplished by subjecting the acoustic wave element already assembled as shown in FIG. 3 to a drying treatment by vacuum dehydration for thereby drying the entire air section 10a and thereafter applying a suitable grease film such as of silicone grease to the entirety of the outer wall of the container to keep the air section in the dry state. The grease film may also be applied thereto after the outer wall of the container has been coated with the molded layer. Besides, the air section 10a can be thoroughly evacuated of air and a damping effect can be imparted thereto by filling the air section to capacity with a polymer material such as silicone resin.

By use of the acoustic wave detector of the construction described above, acoustic waves generated over widely varying temperatures ranging from room temperature to extremely low temperatures can be detected with high stability.

A detector of the type which provides a stable operation at temperatures exceeding room temperature, though not illustrated herein, can be formed by using a wave conductor such as of stainless steel, for example, which is effective in keeping down the degree of acoustic attenuation, and this detector can be effectively used when it is disposed outside the system. Of course in such case, it is desirable to have the detector kept in tight contact with the system, with one end of the wave conductor opposed to the electromagnet and the other end opposed to the detector respectively at positions believed to be suitable for the purpose of measurement.

The method employed for attaching the detector 8 to the electromagnet and other similar factors can be selected freely. The attachment, for example, can be satisfactorily effected by selecting from among various methods available today for causing two mechanical elements destined for use at extremely low temperatures to be closely attached to each other. One suitable method comprises joining the two elements through the medium of silicone grease as a type of adhesive and, as occasion demands, additionally using a cotton tape.

In the superconducting system which is provided with the acoustic wave detector 8 of the foregoing description, when an acoustic wave signal is issued from the superconducting system while the superconducting system is in the process of being cooled to extremely low temperatures or is in its operating state, the acoustic wave detector 8 detects this signal and produces, although very feebly in most cases, an electric output corresponding to the data carried by the acoustic wave signal. Consequently, the information required to determine the identity of the original signal is obtained by having this electric output processed and analyzed in a suitable measuring circuit system 16 of some known operating principle. One example of the measuring system useful for this purpose will be described with reference to the diagram of FIG. 1.

The electric output detected by the acoustic wave detector 8 is quite feeble as already mentioned. It is, therefore, necessary to provide the detector with a band-pass and amplifier 17 which is capable of amplifying this feeble electric output to a suitable magnitude and capable of providing a band-pass filter function for selectively passing the frequency band required for the measurement, especially the portion, falling within a prescribed frequency band, of the acoustic wave signal emitted while an abnormal state of the electromagnets 5a, 5b is developing toward catastrophic quenching, which frequency band includes therein a component corresponding to the medium frequency in the energy distribution of the signal. Thus, the electric output is suitably converted into digital data (not shown), and then delivered to a recorder 19 via a counter 18 adapted to count of pulses exceeding a prescribed level so as to have necessary information stored. The data held in said recorder 19, when necessary, is forwarded to a display 22 such as a pen recorder via a known analyzing mechanism such as a transient phenomenon memory 20 or wave analyzer 21, so that the information may be written out on a chart paper, for example.

The results obtained in a test performed by using the embodiment described above will be described hereinafter in comparison with the results obtained by operating the same system in accordance with the conventional method involving the measurement of voltage.

First in either of the two electromagnets 5a, 5b, the driving current Ea or Eb was allowed to flow at a fixed increasing rate and an abnormal state brought about in consequence of the increased driving current was kept under observation to determine how said abnormal state would develop into catastrophic quenching. The results are shown in FIG. 5. FIG. 5(A) shows the driving current being automatically increased at a fixed rate of 0.5A per second. FIG. 5(B) shows the frequency and intensity (absolute values are meaningless for the purpose of explanation and are omitted herein) of the acoustic wave signal (having about 3 MHz of medium frequency) detected by the acoustic wave detector incorporated in the embodiment under discussion. FIG. 5(C) shows the results of the operation of the superconducting system of FIG. 1 in accordance with the conventional method involving the measurement of voltage.

The data of FIG. 5 may be comprehended more easily by assuming the curves to represent loci recorded on chart papers. A review of the data of the acoustic wave signal emitted by either of the electromagnets 5a, 5b involved in the system of this invention reveals that the frequency of the signal begins to rise and the intensity thereof also begins to increase at the point "P" (representing an age of about 180 seconds of the flow of the driving current) on the time axis "t." This means that occurrence of an abnormal state in the functional element is observable at or after the point "P." About 10 seconds after this point, at the position indicated by the segment Q—Q, an abrupt decline in current is shown in FIG. 5(A), clearly indicating the occurrence of the phenomenon of quenching. That is to say, in accordance with the present invention, the abnormal state preceding the catastrophic quenching can be definitely detected through observation of an abnormality which shows itself at the point "P" of the time axis. Thus, the detection which is accomplished as described above permits one to tell that the abnormal state is developing toward the phenomenon of quenching and also to determine the extent of the growth of the abnormal state without having to expose the electromagnet to the actual danger of quenching. A study of the results of FIG. 5(C) obtained by the method involving the measurement of voltage reveals that no definite sign of abnormality can be foretold and the presence of an abnormal state cannot be recognized until it has developed into catastrophic quenching. It is noted that absolutely no early sign is detected between the points P and Q. This clearly demonstrates the effectiveness of the present invention in the early detection of such an abnormal state.

Further, the present invention not merely permits the occurrence of an early sign (Point P) of quenching to be detected on the basis of the frequency and intensity of the acoustic wave signal but also provides more detailed information on the abnormal state.

Figure 6A:
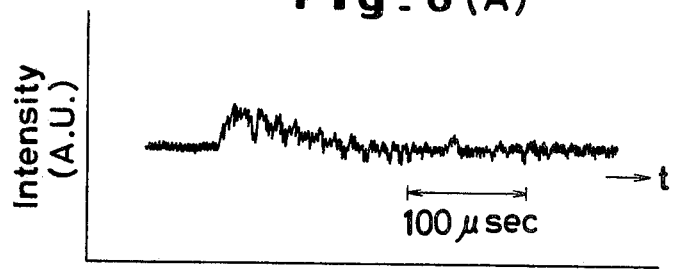
FIG. 6 is a graph showing in a magnified scale parts of the curves in the graph of FIG. 5(B).
Figure 6B:
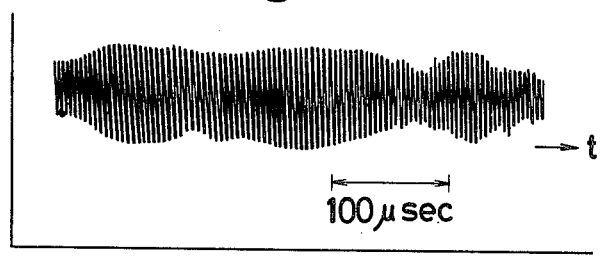

In the case of the data of FIG. 5(B), for example, although the portion of the curve near the point P appears to be a one-shot locus, it is noted that one of the various acoustic wave signals has a wave form like the one illustrated in FIG. 6(B) when it is elaborately inspected microscopically by enlarging the time axis. Since the point P is known from the curve of FIG. 5(B) to represent the time at which the abnormal state as a forerunner of quenching occurs, it is logical to conclude that this wave form represents an early sign preceding actual catastrophic quenching.

Figure 6C:
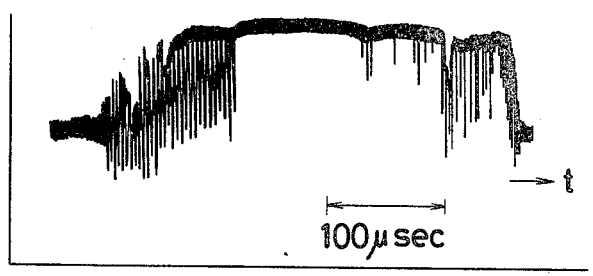

In FIG. 5(B) which shows the results of the test continued until the occurrence of catastrophic quenching, a microscopic inspection of the various acoustic wave signals in the portions near the point Q immediately preceding the phenomenon of quenching reveals wave forms like those of FIG. 6(C).

It is therefore safe to conclude that the abnormal state is still in a stage of an early sign so far as the wave forms of FIG. 6(B) are obtained and that the system as a whole may be regarded as functioning normally before the appearance of the wave forms of FIG. 6(C). Proper remedial operations and countermeasures for the elimination of such an abnormal state can be carried out, therefore, before the abnormal state attains full growth into catastrophic quenching.

A similar careful inspection of one of the signals occurring at a lower frequency at a given point P' prior to the point P in FIG. 5(B) reveals wave forms like those shown in FIG. 6(A).

In the light of the wave forms of FIG. 5(B), this point P' does not suggest the presence of any problem from the operational standpoint of the system.

When there is issued an acoustic wave signal involving such wave forms, these negatively exponential wave forms which clearly differ from the wave forms representing an early sign as shown in FIG. 6(B) permit one to tell that the abnormal state is still in the stage of an early sign or in a stage even preceding that of the early sign. In other words, the abnormal state is still in the form of a feeble sign of abnormality.

When a microscopic inspection is continued along the course of time as in the curves of FIG. 6, the correspondence among wave forms can be determined and the proper countermeasures for the elimination of the abnormal state can be carried out as described below.

Since the wave forms of the acoustic wave signal at the point P' are negatively exponential as illustrated in FIG. 6(A), the occurrence of such an acoustic wave signal does not necessarily dictate adoption of a proper countermeasure but may well serve as a "warning signal" from the standpoint of the system as a whole. So far as these wave forms are present, the driving currents to the electromagnets can safely be delivered at the initially fixed increasing rate.

Even if the wave forms continue to drag over a long period of time as shown in FIG. 6(B), they merely indicate that the abnormal state is still in the stage of an early sign at the point P of FIG. 5 and that there is no need for promptly cutting off the magnet current. When there is to be adopted a countermeasure of the nature of a remedial operation, possible breakdown of the system can be precluded by decreasing the increasing rate of magnet current flow or by temporarily discontinuing the increase of electric current and keeping the current flow at a fixed level, for example. That is to say, the operation of the system can safely be continued so long as the wave forms of FIG. 6(B) are present.

When, in the course of the monitoring, there appear wave forms like those of FIG. 6(C), they indicate that the abnormal state has approached the stage immediately preceding that of the phenomenon of quenching. In this case, the system can be protected against breakage by promptly cutting off the flow of electric current or by decreasing the flow of current.

By close time-course inspection of the wave forms of the acoustic wave signal issuing from the system, an abnormal state in the stage of an early sign or in a stage preceding that of the early sign can be detected. As a way for comprehensive monitoring of the superconducting system, no known methods can compare favorably with that of the present invention.

While one of the two electromagnets was kept in permanent current mode and the other electromagnet was kept in operation, the driving current to the operated electromagnet was delivered at an increasing rate and an abnormal state brought about in consequence of the increased driving current was kept under observation to determine how the abnormal state would develop into catastrophic quenching. The results are shown in FIG. 7. For the sake of comparison with the results shown in FIG. 5, the electric current indicated in FIG. 7 is calculated at the same fixed increasing rate and the points of quenching are invariably indicated by a segment Q—Q in the relevant curves.

As shown in FIG. 7(B), the device of the present invention is not affected in any way by a separate superconducting electromagnet which happens to be disposed nearby and it gives the same results as those shown in FIG. 5(B). The sign of quenching which appears after the point P can be detected accurately as it is by this device. In the case of the conventional method involving the measurement of voltage, however, the presence of a separate electromagnet in the neighborhood produces a direct influence in the form of an overlapping magnetic field, with the result that the voltage signal detected by this method will describe a complicated loci as illustrated in FIG. 7(C). It is altogether impossible to determine from the data of FIG. 7(C) whether the voltage increase appearing near the point x, for example, is a manifestation of an abnormal state in the stage of an early sign of the phenomenon of quenching or a background noise originating in the mutual inductance between the electromagnets or in the lack of uniformity in the diffusion of magnetism.

An inspection of the wave forms of acoustic wave signals which issued when the two electromagnets were operated as described above revealed the presence of wave forms approximately equalling those shown in FIG. 6(A), (B) and (C) at the points Q, P and P' of FIG. 7 corresponding to those of FIG. 5. This clearly indicates that no effect of external magnetic flux appears even in the microscopic inspection.

So far, the description has been limited to the situation wherein one of the two electromagnets involves an abnormal state which is an early sign of quenching. Of course, by use of the embodiment illustrated in FIG. 1, real-time monitoring can be effected on the simultaneous operation of both electromagnets. When the monitoring detects changes of acoustic wave signals during the interval from the point P to the point Q as shown in FIG. 5 and FIG. 7, then the proper remedial operations described above can be made or proper countermeasures taken by the medium of a suitable control system amply in time for precluding the abnormal state from attaining full growth into catastrophic quenching.

The exact point at which an abnormal state occurs within the superconducting system can be detected by means of a plurality of acoustic wave detectors disposed at suitable positions on each electromagnet. Since an acoustic wave signal emitted from a given point of trouble is naturally conveyed at the constant speed of sound and paths followed by the signal wave from the point of trouble to the various detectors differ in length from one another, the lengths of paths from the various detectors to the point of trouble can be conversely computed from the differences in intensity, time interval and phase due to said different lengths of paths which are detected by the various detectors. Thus, the exact point of trouble can be accurately located in much the same way as in the seismologic location of the origin of earthquake.

It is believed that the effectiveness of the present invention in the monitoring of the superconducting system against occurrence of abnormal phenomena as possible forerunners of catastrophic quenching is quite evident from the description given to this point.

While the conventional method which is incapable of direct detection of nascent voltage fails to detect the kind of damage done to the superconductor proper or to the component members thereof by an interrupting current, the method of the present invention can detect this damage by establishing, through the medium of a measuring system not illustrated but similar to that described above, necessary correspondence between the damage involved and the intensity and frequency of the sound waves of the acoustic wave signal issued consequently. It is further capable of evaluating the type of the construction and the material itself through additional mathematical processing.

Besides, the detection of such an abnormal state as loss of balance in the cooled condition can be accomplished by use of a measuring system like that illustrated in FIG. 1.

Take, for instance, the case in which the container of the superconducting system is monitored for its cooled condition. In the construction of FIG. 1, a suitable number of acoustic wave detectors 8' (only one such detector shown in the drawing) indicated by imaginary lines may be disposed in intimate contact therewith, for example. If loss of balance occurs in the cooled condition, the condition, extent and exact spot of strain produced in the container can be determined as by spectrally analyzing the acoustic wave signal with respect to its frequency components or by recording the intensity, frequency and wave form of acoustic waves involved. Desired uniformization of the speed of cooling can be attained by continuing the monitoring throughout the entire precooling process. Even during the actual operation of the superconducting system, any strain generated in the container by an external factor can be detected through this monitoring.

Here, attention is invited to the inventors' experiment performed by use of a superconducting system (incorporating therein electromagnets 100 mm in inside diameter, 200 mm in outside diameter and 2100 mm in height) to determine the relation between the history of the cooling continued to the prescribed cryogenic level of 4.2 K. and the intensity and frequency of the acoustic wave signal emitted during the interval. Typical results obtained by this experiment are shown in FIGS. 8(A) through (E).

Figure 8A:
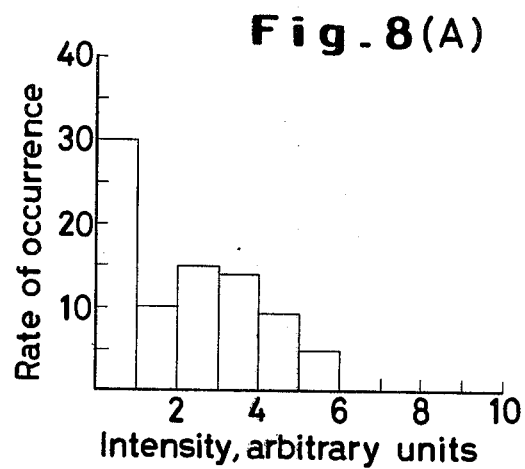
FIG. 8 is a graph showing the intensity-to-frequency relationship of the acoustic wave signals to be detected while the system of FIG. 1 is cooled to extremely low temperatures.
Figure 8B:
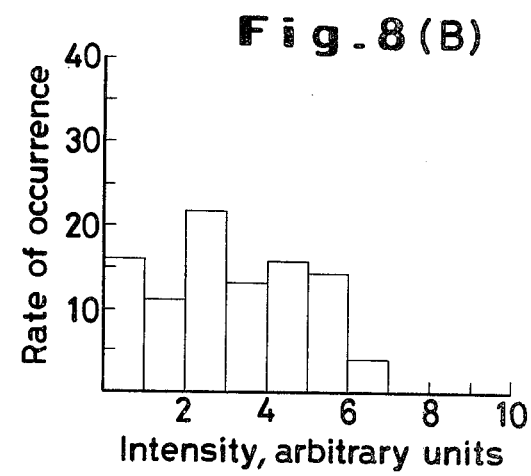
Figure 8C:
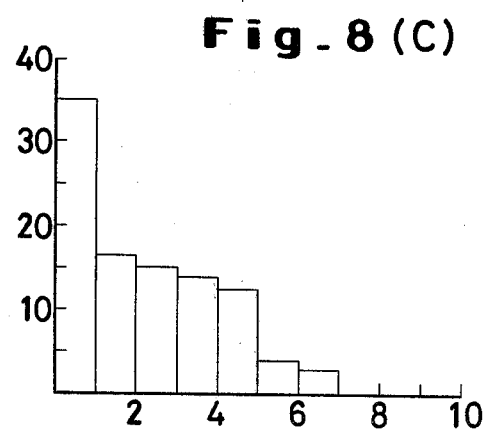
Figure 8D:
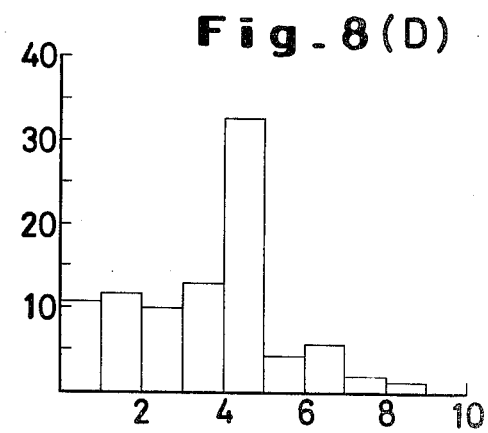
Figure 8E:
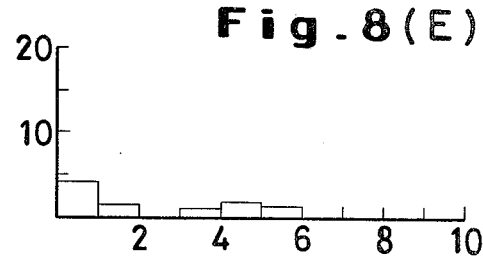

FIG. 8(A) represents the data obtained in the temperature interval of 300–230 K., FIG. 8(B) those in the temperature interval of 230–150 K., FIG. 8(C) those in the temperature interval of 150–100 K., FIG. 8(D) those in the temperature interval of 100–20 K. and FIG. 8(E) those in the temperature interval of 20–4.2 K., respectively for a fixed sample duration of 10 minutes.

Once necessary data are thus collected about normal cooling of the system to the cryogenic level, if the results obtained with an identical or similar system in any of the temperature intervals are found to differ vastly from those shown in the diagrams of FIG. 8 (for example, occurrence of acoustic waves of relatively high intensity at a high frequency) can safely be concluded as an indication that there has occurred unbalanced thermal contraction within the system under investigation.

Of course in this case, the safest measure that can be taken to cope with the situation will be by returning the temperature to the original normal level and giving the system a thorough inspection. Required correction of the situation may otherwise be attained by examining the cooling speed and properly adjusting it so as to eliminate the abnormal results and eventually reduce them to those of patterns similar to those shown in the diagrams of FIG. 8(E).

What has been described so far is true not only of the container itself but also of all the component members of the system. The signals which are detected by the acoustic wave detectors 8 disposed on the functional elements such as electromagnets 5a, 5b include those bearing the kinds of information indicative of the aforementioned unbalanced cooling condition. This means that, in addition to permitting the monitoring of the system against occurrence of abnormal phenomena which may lead to quenching, the same detector elements (theoretically capable of being provided independently, as a matter of course) can be used for the purpose of ensuring uniformization of the cooling condition. These detectors can be disposed on those parts which are acoustically connected to the relevant component members subjected to monitoring instead of being directly connected to the component members. For example, in monitoring the container, fully satisfactory results are obtained by attaching the detectors to the supporting devices serving to hold the functional elements fast against the container. Even with the detectors 8 which are provided on the functional elements, abnormal phenomena occurring in the container can be detected. For the purpose of directly detecting such abnormal phenomena while excluding all possible external influences as much as possible, however, it is more advantageous to have the detectors directly provided on the component members subjected to monitoring (as, for example, by attaching detectors 8' directly to the container where the component member subjected to monitoring happens to be a container as illustrated).

Now, a specific measuring unit of the structure of FIG. 1 designed to bring about results identical with or similar to the results of measurement involved in the monitoring and control of the superconducting system and shown in FIGS. 5 through 8 and a typical automatic control unit designed to be operated in accordance with the output data from said measuring unit will be described with reference to FIGS. 9 through 12.

In FIGS. 9 through 12, like component members of the superconducting system and the acoustic wave detectors illustrated in FIG. 1 are indicated by like numeral symbols. FIG. 9 illustrates a measuring circuit system 16 of the present embodiment. Measuring circuit system 16 can be attached to each of the detectors 8 which are disposed, one each, in tight contact with a toroidally wound electromagnet 5a and a poroidally wound electromagnet 5b. In the present embodiment, the description will be limited to the measuring circuit system 16 disposed on the detector 8 which is attached to the toroidally wound electromagnet 5a for the sake of brevity.

The signal issuing from the detector 8 is generally very feeble and, therefore, is suitably amplified by means of a preamplifier 23. With the aid of a band presetter, the amplified signal is passed through a band-pass filter 24 which is capable of selecting a desired center frequency, so as to select out the portion of the signal in a desired band width corresponding to the portion having a center frequency of 3 MHz at the aforementioned detector 8. The selected signal is then amplified by a main amplifier 25 up to an appropriate level as required for the processing for the purpose of measurement. In this embodiment, the output signal issuing from the main amplifier 25 is forwarded to the Schmidt circuit 26, a peak hold circuit 27 and a comparator 28.

The signal received in the Schmidt circuit 26 is converted into pulses and the signal pulses are forwarded via a clock pulse gate 29 incorporating an AND circuit to a counter 30, wherein the frequencies of acoustic wave emission (A.E.) are determined. These frequencies of occurrence may be printed out by a suitable printer 31 for future reference or displayed by a suitable display device 32 for direct visual inspection.

If the data are to be handled by an automatic control unit (illustrated in detail in FIG. 10) which will be described afterward, it is compared by a comparator 33 whether or not the measured frequency Cs exceeds the preset frequency Cp. A program will be used so that the unit gives an output [1]) when the measured frequency Cs exceeds the preset frequency Cp or an output [0] when the former does not reach the latter. It should be noted at this point that the actual value of this preset frequency Cp will be empirically determined on the basis of the frequency of occurrence of the acoustic wave signal which may be emitted during the operation of the superconducting system at the point at which an abnormal state occurs as an early sign of catastrophic quenching (near the point P in FIG. 5) or, where ample allowance is given for safety, at a point prior to said point (near the point P'), for example.

The output signal issuing from the main amplifier 25 is also forwarded to the peak hold circuit 27, wherein the peak values of the output signal are successively detected. These peak values may be registered by a recorder 34 for future reference or displayed by a suitable display device (either a peak meter or a digital peak display device using a photodiode and a digital display) for direct visual inspection. If the peak values thus determined are to be handled by an automatic control unit described afterward, there will be incorporated logical circuits so designed that, while the peak values of signal are being detected by the peak hold circuit 27, the amplitude of signal Ps is compared with the preset amplitude level $P_p$ by means of a comparator 35 to give rise to an output [2] when the former exceeds the latter or an output [0] when the former fails to reach the latter. As the preset peak value or intensity (amplitude), the peak value of the acoustic wave signal emitted near the point P or, where absolute safety is desired, the peak value of the signal emitted prior to the point P must be used.

As concerns the part of the wave form of the output signal issuing from the main amplifier 25 which exceeds a fixed level, said signal is passed through a comparator 28 designed to compare the signal with said fixed level and subjected to a suitable A/D conversion by means of an A/D converter 36. Thereafter, the part of wave form in excess is committed to storage in the wave memory 37 and, at the same time, displayed by a synchroscope 38 for direct visual inspection. At the same time the frequency of this particular signal is analyzed by a frequency spectral analyzer 39.

The wave forms of signals which appear in the synchroscope 38, on observation, are found to be similar to those illustrated in FIGS. 6(A), (B) and (C). For said automatic control unit to be effectively adopted for the handling of these wave forms, there will be incorporated a program such that whenever the analyzer 39 determines a frequency distribution corresponding to the wave forms of a given signal, there is produced by detecting the main frequency level Fs with detectors 40 and 41 an output [3] when the main frequency level Fs found in said frequency distribution falls within the first preset level band range ($F_1 <$ Fs $\leq F_2$) or an output [4] where said main frequency level Fs exceeds the first preset level band range ($F_2 <$ Fs). Thus, the wave forms (shown in FIG. 7(B)) at the point P in FIG. 5 can be identified as those whose main frequency level gives rise to the output [4] and the wave forms (shown in FIG. 7(B)) at the point P' as those whose main frequency level gives rise to the output [3] respectively, for example.

FIG. 10 depicts one example of the automatic control unit which makes use of such output signals as described above.

In the illustrated embodiment, the outputs [1], [2], [3], [4] and [0] issuing from the measuring circuit system 16 for superconducting magnet current control are fed as inputs to the logic circuit 42 which is a suitable combination of AND/OR circuits so as to produce an output signal in one of a total of six current operational Modes I through VI, selected in accordance with whether a relevant output is present or absent or which of the two values of binary notation is produced, for example. The Modes to be used in this operation may be defined as follows, for example:

Mode I: (Go on)

For the flow of magnet current I to be continued at the initially preset current increasing rate $C_0$.

Mode II: (Go up slower)

For the flow of magnet current I to be continued at an increasing rate lower than the initially preset increasing rate $C_0$.

Mode III: (Hold)

For the flow of magnet current I to be continued at a constant rate, with the initially preset increasing rate $C_0$ nullified.

Mode IV: (Go down slower)

For the flow rate of magnet current to be lowered gradually at a decreasing rate which is not required to exceed the relatively preset decreasing rate $C_1$.

Mode V: (Go down fast)

For the flow of magnet current to be continued at a decreasing rate greater than the prescribed decreasing rate $C_1$, so as to effect the decrease of current flow rapidly.

Mode VI: (Cut off)

For the flow of magnet current to be immediately discontinued.

The correspondence between the inputs [1], [2], [3], [4] and [0] and the output Modes I, II, III, IV, V and VI is as described below.

When the input [0] alone is received, the output is in Mode I, causing the pertinent power supply 7 to continue the supply of magnet current to the pertinent electromagnet 5a at the prescribed current increasing rate $C_0$.

When either of the outputs [1] and [2] is received, the output is given off in Mode II, causing the power supply 7 to lower the initially preset current increasing rate.

If the outputs [1] and [2] are both received, this is an indication that the situation is now in need of proper, if not too serious, attention. In this case, therefore, the output is in Mode III, for example, causing the supply of magnet current to be continued at the rate existing at that moment.

When the inputs [1], [2] and [3] are received, the output is in Mode IV, causing the current increasing rate to be decreased as occasion demands.

If the inputs [1], [2] and [4] are received, this is an indication that there has appeared a main frequency level deviating from the first preset range. In this case, therefore, the output is in Mode V which causes the decrease of the flow of magnet current to proceed more rapidly than in Mode IV.

If the outputs [1], [2], [3] and [4] all appear frequently or persist for a period longer than the prescribed duration, this is an indication that the abnormal state has grown to a stage immediately preceding the point of catastrophic quenching. In this case, the output is given off in Mode VI, causing the power supply 7 to be cut off without loss of time. It is self-evident that a circuit having an absorption resistance 43 and a diode 44 arranged therein in serial connection can be inserted in parallel to the electromagnet 5a if the inserted circuit enables the energy retained within the electromagnet 5a to be safely absorbed.

Figure 11:
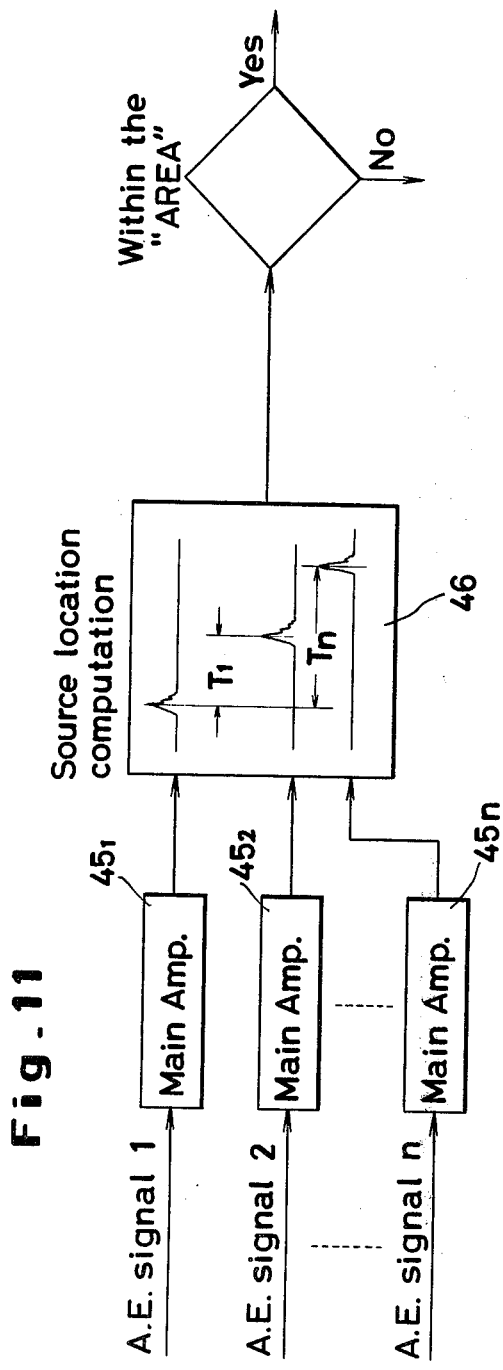
FIG. 11 is a circuit view showing one example of a circuit system for monitoring the superconducting system which is provided with a plurality of detectors.

For more accurate location of spots of trouble in the superconducting system by means of multiple channels using a plurality "n" of detector 8, it is advantageous to adopt a method which involves use of an arrangement illustrated in FIG. 11 in addition to the measuring unit described above. By this method, desired location of source of trouble can be attained by allowing the A.E. signals 1 through n issuing from the varying detectors to be passed through the corresponding main amplifiers $45_1$ through $45_n$ and causing the relevant time lags $T_1$, $T_2$ to be detected by the source-location computation device 46. Thus, the ease with which the trouble-shooting is effected can be all the more enhanced. Of course, it is desirable that this operation should be capable of determining whether or not the main frequency levels of the detected signals fall within the fixed area. This is because the detectors have an undeniable possibility of picking up some extraneous sound.

Figure 12:
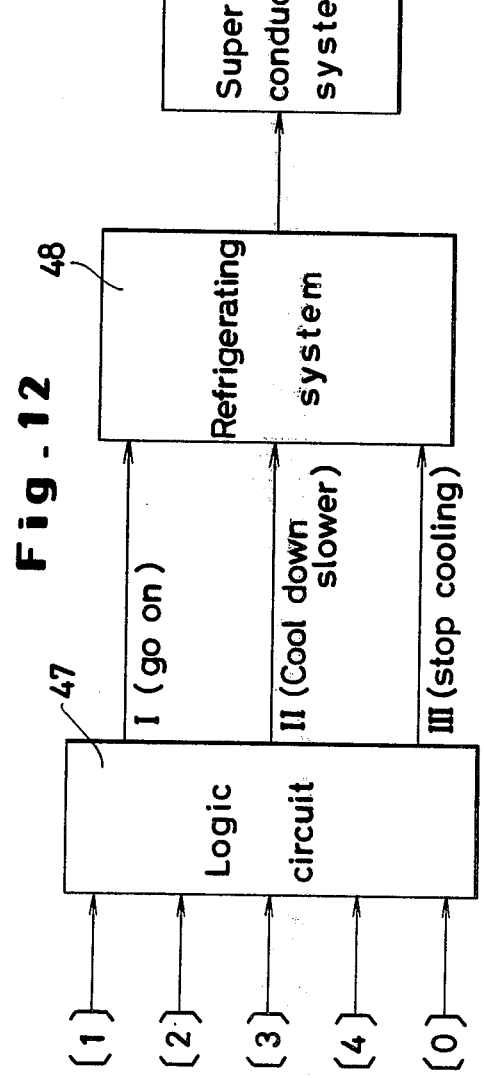
FIG. 12 is a circuit view showing the state in which a cooling system is monitored in cooling the superconducting system.

By use of the output signals from a measuring circuit system like that shown in FIG. 9, the superconducting system can be monitored and controlled while it is being cooled to extremely low temperatures. FIG. 12 is a conceptual diagram representing one example of this operation.

Desired control of the cooling device 48 of the superconducting system 1 is accomplished advantageously by means of a logic circuit 47 for refrigenating system which is composed of suitable logic circuits in such a way that the output signals from the measuring circuit system will be given off in Modes I, II and III which may be defined as follows, for example:

Mode I: (Go on)

For the cooling of the superconducting system to be continued at the prescribed cooling rate.

Mode II: (Cool down slower)

For the cooling speed to be lowered down.

Mode III: (Stop cooling)

For the cooling to be stopped.

The correspondence between the inputs [1], [2], [3], [4] and [0] and the output Modes I, II and III is fixed as described below, for example.

In the measuring circuit system 16 of FIG. 9, the values of $C_p$, $P_p$, $F_1$ and $F_2$ are fixed so that the safety of the system is guaranteed until the cooling of the system is brought to completion.

When the input [0] is received, the output is naturally given off in Mode I.

When either or both of the two inputs [1] and [2] or the three inputs [1], [2] and [3] are simultaneously received, the output is given off in Mode II, causing the cooling rate to be lowered.

When the input [4] is received, the output is given off in Mode III, causing the cooling to be immediately stopped.

To allow for added safety, there can readily be conceived the idea of modifying said correspondence between the inputs and the output Modes so that the output will be given off in Mode II when either of the inputs [1] and [2] is received and in Mode III when said two inputs are received simultaneously, no matter whether the inputs [3] and [4] are received or not.

Though the description has so far been limited to the detection of acoustic waves by means of the detector 8 disposed on the electromagnet 5a, similar detection of acoustic waves can be attained by having the detector provided on the electromagnet 5b.

As described in full detail above, the present invention has many outstanding effects as enumerated below.

(i) Since the signals subjected to measurement have already undergone conversion to acoustic field, they are not affected, disturbed or otherwise impaired electrically or magnetically. Thus, the electromagnetic devices in the superconducting system are not affected by the manner of energization of electromagnets, mutual inteference of magnetic fluxes, and so on. Even in the magnetic field involving application of powerful magnetism and entailing heavy variation of time element, required detection and measurement can be obtained without any trouble. In a supplementary sense, the sensitivity of the monitoring device can easily and safely be heightened to a desired level.

(ii) Signs of abnormal phenomena as possible forerunners of quenching can be detected well in time for proper measures to be taken for preventing the superconducting electromagnets from catastrophic quenching and consequently avoiding destructive release of magnetic energy. Further, feeble signs of oncoming abnormal phenomena can be detected. If this invention is used in the test of superconducting electromagnets of great dimensions prevalent today, for example, the stability of performance of such electromagnets can be detected and evaluated without intentionally allowing abnormal phenomena to develop into catastrophic quenching. As a real-time non-destructive testing method, therefore, this invention proves to be high effective.

(iii) Strains due to unbalanced cooling conditions can be quantitatively detected. In the precooling process, for example, desired uniformization of the cooling speed can easily be attained. This invention, therefore, provides evaluation of the component members of the system and prevention of these component members from unexpected damage.

(iv) Loss of stability of electromagnets due to an interruption of current can also be detected.

(v) Origins of acoustic wave signals, namely, points of abnormal phenomena leading to quenching can be accurately located by means of a plurality of detectors disposed at suitable positions. For example, growth of strains can be observed. Thus, this invention is useful for the purpose of maintenance and management of functional elements and the system as a whole and early detection of spots of trouble as well as for experimental purposes.

As described above, the present invention provides a comprehensive means of detection and analysis of abnormal phenomena of some form or other which may possibly occur within the superconducting system. Thus, it is expected to find extensive utility in applications to superconducting electromagnetic systems (such as, for example, magnetic devices designed to keep linear motors buoyant while in motion), M.H.D. power generation, nuclear fusion, high-energy accelerating devices, electric charge bending electromagnets, and so on.

What is claimed is:

1. A method for monitoring a superconducting system comprising the steps of:
    disposing at least one acoustic wave detector at a functional element of the superconducting system;
    detecting an acoustic wave signal emitted upon occurrence of a deviation from the superconducting state within said superconducting system;
    comparing a characteristic of the acoustic wave signal with a predetermined value; and
    giving to the superconducting system a corrective measure selected in accordance with the characteristic of the acoustic wave signal detected by said acoustic wave detector to eliminate the deviation from the superconducting state.

2. The method according to claim 1, including the step of:
    measuring the frequency, intensity, frequency of occurrence and wave forms of the detected acoustic wave signal.

3. A device for monitoring a superconducting system, which comprises:
    at least one acoustic wave detection means provided at a functional element of the superconducting system for detecting acoustic wave signals emitted upon occurrence of a deviation from the superconducting state within the superconducting system; and
    control means for comparing a characteristic of the acoustic wave signal with a predetermined value and ginving to the superconducting system a required corrective measure selected in accordance with the characteristic of the acoustic wave signal to eliminate the deviation from the superconducting state.

4. The device according to claim 3, wherein the superconducting system is provided with a plurality of acoustic wave detectors.

5. The device according to claim 4, wherein the superconducting system is disposed at extremely low temperatures.

6. The device according to claim 4, wherein the acoustic wave detectors are provided on the functional elements of the superconducting system.

7. The device according to claim 4, wherein the acoustic wave detectors are provided on the supporting devices serving to hold the functional elements fast against the superconducting system.

8. The device according to claim 4, wherein the acoustic wave detectors are of a type which operates stably under extremely low temperature conditions.

9. The device according to claim 3, wherein the control means is capable of analyzing the output signal of the acoustic wave detectors with respect to frequency, intensity, frequency of occurrence and wave forms.